(12) United States Patent  (10) Patent No.: US 9,936,907 B2
Liao et al.  (45) Date of Patent: Apr. 10, 2018

(54) APPARATUS AND METHOD FOR PROCESSING PHYSIOLOGICAL SIGNAL (71) Applicants: LITE-ON ELECTRONICS (GUANGZHOU) LIMITED, Guangzhou (CN); LITE-ON TECHNOLOGY CORPORATION, Taipei (TW)

(72) Inventors: Ching-Huan Liao, Taipei (TW); Ching-Feng Cheng, Taipei (TW)

(73) Assignees: LITE-ON ELECTRONICS (GUANGZHOU) LIMITED, Guangzhou (CN); LITE-ON TECHNOLOGY CORPORATION, Taipei (TW)

( * ) Notice: Subject to any disclaimer, the term of this patent is extended or adjusted under 35 U.S.C. 154(b) by 244 days.

(21) Appl. No.: 14/583,293

(22) Filed: Dec. 26, 2014

(65) Prior Publication Data

US 2016/0106351 A1   Apr. 21, 2016

(30) Foreign Application Priority Data

Oct. 20, 2014   (CN) .......................... 2014 1 0560147

(51) Int. Cl.
*A61B 5/1455* (2006.01)
*A61B 5/00* (2006.01)
(Continued)

(52) U.S. Cl.
CPC .......... *A61B 5/14552* (2013.01); *A61B 5/015* (2013.01); *A61B 5/02433* (2013.01);
(Continued)

(58) Field of Classification Search
CPC ........ A61B 2562/0238; A61B 2576/00; A61B 2576/02; A61B 5/004; A61B 5/015;
(Continued)

(56) References Cited

U.S. PATENT DOCUMENTS

2002/0118865 A1* 8/2002 Hosokawa ......... G06K 9/00013
382/124
2005/0053264 A1* 3/2005 Amano ................ G06K 9/0002
382/115

(Continued)

*Primary Examiner* — Yong Hang Jiang
(74) *Attorney, Agent, or Firm* — Li & Cai Intellectual Property (USA) Office (57) ABSTRACT A physiological signal processing apparatus and a method for the same. The physiological signal processing apparatus includes a first light-emitting element, a second light-emitting element, a light control module, an image sensing module and an analyzing module. The light control module is capable of controlling the first light-emitting element to emit a first light beam and the second light-emitting element to emit a second light beam on a light guide panel for a finger to touch. The image sensing module is capable of sensing the first light beam and the second light beam reflected by the light guide panel and acquiring an image signal of the finger. The analyzing module is capable of analyzing the image signal extracted by the first light beam to acquire a first physiological signal and analyzing the image signal extracted by the second light beam to acquire a second physiological signal.

18 Claims, 4 Drawing Sheets (51) Int. Cl.
*A61B 5/117* (2016.01)
*A61B 5/01* (2006.01)
*A61B 5/1172* (2016.01)
*A61B 5/024* (2006.01)
*A61B 5/0205* (2006.01)

(52) U.S. Cl.
CPC ............. *A61B 5/1172* (2013.01); *A61B 5/004* (2013.01); *A61B 5/02055* (2013.01); *A61B 5/7221* (2013.01); *A61B 2562/0238* (2013.01); *A61B 2576/00* (2013.01); *A61B 2576/02* (2013.01)

(58) Field of Classification Search
CPC ............ A61B 5/02055; A61B 5/02433; A61B 5/1172; A61B 5/14552; A61B 5/7221
USPC ................................................. 340/5.52, 5.53
See application file for complete search history.

(56) References Cited

U.S. PATENT DOCUMENTS

2008/0226137 A1* 9/2008 Benaron .............. G06K 9/0012
382/115
2009/0033937 A1* 2/2009 Oh ...................... A61B 5/02433
356/366

* cited by examiner

APPARATUS AND METHOD FOR PROCESSING PHYSIOLOGICAL SIGNAL

BACKGROUND

1. Technical Field

The present invention generally relates to a recognition apparatus and a recognition method and, more particularly, to an apparatus and a method for recognizing physiological characteristics.

2. Description of Related Art

Generally, in a multi-functional recognition equipment for physiological characteristics, capacitive sensors are usually used to recognize a fingerprint, photo-electronics sensors are used to recognize the palpitant frequency and the blood oxygenation, and far infrared (FIR) sensors are used to sense the human body temperature. Therefore, currently available recognition equipment has to be provided with corresponding sensors to recognize various physiological characteristics. For manufacturers or suppliers, installing more sensors in recognition equipment adds more assembly complexity and higher material cost. Therefore, further development of improved recognition equipment has attracted tremendous attention.

SUMMARY

One embodiment of the present invention provides a physiological signal processing apparatus. The physiological signal processing apparatus includes a first light-emitting element capable of emitting a first light beam and a second light-emitting element capable of emitting a second light beam. The first light-emitting element and the second light-emitting element emit the first light beam and the second light beam on a light guide panel for a finger to touch. The first light-emitting element and the second light-emitting element are disposed opposite to where the finger touches the light guide panel. The physiological signal processing apparatus further includes a light control module, an image sensing module and an analyzing module. The light control module controls the first light-emitting element and the second light-emitting element to emit the first light beam and the second light beam. The image sensing module senses the first light beam and the second light beam reflected by the light guide panel to provide an image signal of the finger. The analyzing module analyzes the image signal extracted by the first light beam to acquire a first physiological signal, and analyzes the image signal extracted by the second light beam to acquire a second physiological signal. The first physiological signal is different from the second physiological signal.

One embodiment of the present invention further provides a physiological signal processing apparatus. The physiological signal processing apparatus includes a light source module, a light control module, an image sensing module and an analyzing module. The light source module is capable of emitting a mixed light beam on a light guide panel for a finger to touch. The light source module is disposed opposite to where the finger touches the light guide panel. The mixed light beam includes a plurality of colored light beams. The light control module is coupled to the light source module and controls the light source module to emit the mixed light beam. The image sensing module senses the mixed light beam reflected by the light guide panel to provide an image signal of the finger. The analyzing module is coupled to the image sensing module and analyzes the image signal extracted by any of the plurality of colored light beams to acquire a plurality of physiological signals.

One embodiment of the present invention provides a physiological signal processing method applicable to the physiological signal processing apparatus. The physiological signal processing apparatus includes an image sensing module. The physiological signal processing method includes steps as follows. At least one first light beam and at least one second light beam are emitted. The image sensing module senses an image signal of a finger on a light guide panel of the physiological signal processing apparatus. The image signal is provided by the first light beam and the second light beam that are reflected. The image signal is analyzed to acquire at least one first physiological signal and at least one second physiological signal. The first physiological signal is different from the second physiological signal.

Accordingly, the present invention provides a physiological signal processing apparatus and a method thereof, in which light-emitting elements are controlled to emit light with different wavelengths and an image signal with respect to a corresponding colored light beam is sensed to be extracted to recognize physiological characteristics. With the use of the present invention, one or more physiological characteristics of a finger can be recognized using the same image signal and the accuracy as well as the efficiency for recognizing physiological characteristics can be improved using the image signal provided by different colored light beams.

In order to further understand the techniques, means and effects of the present disclosure, the following detailed descriptions and appended drawings are hereby referred to, such that, and through which, the purposes, features and aspects of the present disclosure can be thoroughly and concretely appreciated; however, the appended drawings are merely provided for reference and illustration, without any intention to be used for limiting the present disclosure.

BRIEF DESCRIPTION OF THE DRAWINGS

The accompanying drawings are included to provide a further understanding of the present disclosure, and are incorporated in and constitute a part of this specification. The drawings illustrate exemplary embodiments of the present disclosure and, together with the description, serve to explain the principles of the present disclosure.

DESCRIPTION OF THE EXEMPLARY EMBODIMENTS

Reference will now be made in detail to the exemplary embodiments of the present disclosure, examples of which are illustrated in the accompanying drawings. Wherever possible, the same reference numbers are used in the drawings and the description to refer to the same or like parts.

(Embodiment of Physiological Signal Processing Apparatus)

Figure 1:
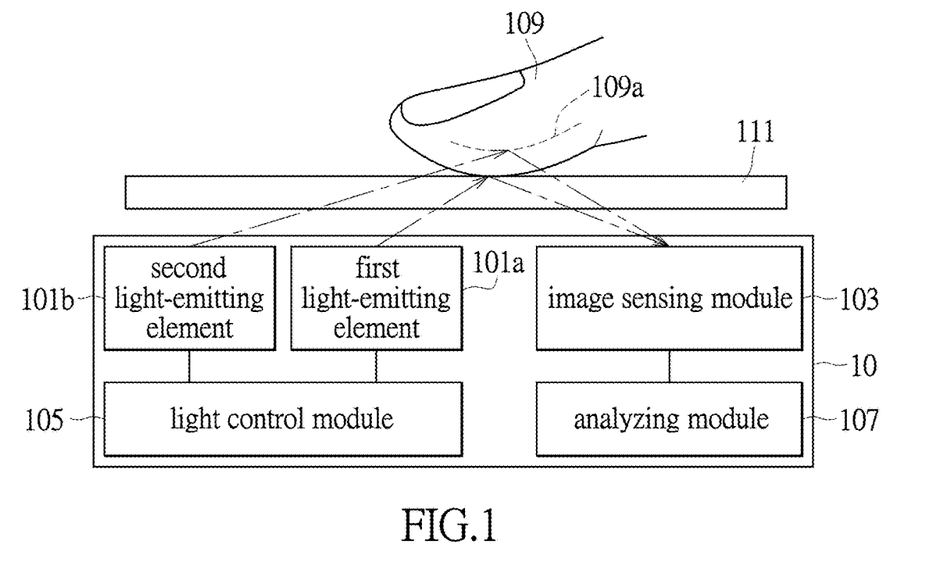
FIG. 1 is a schematic diagram of a physiological signal processing apparatus according to a first embodiment of the present invention.

FIG. 1 is a schematic diagram of a physiological signal processing apparatus according to a first embodiment of the present invention. With reference to FIG. 1, a physiological signal processing apparatus 10 includes a first light-emitting element 101a, a second light-emitting element 101b, a light control module 105, an image sensing module 103 and an analyzing module 107. The first light-emitting element 101a and second light-emitting element 101b are respectively coupled to the light control module 105. The image sensing module 103 is coupled to the analyzing module 107. The physiological signal processing apparatus 10 further includes a light guide panel 111 for a finger 109 of a user to touch. The first light-emitting element 101a and the second light-emitting element 101b are disposed opposite to where the finger 109 touches the light guide panel 111.

The first light-emitting element 101a is capable of emitting a first light beam, and the second light-emitting element 101b is capable of emitting a second light beam. In one embodiment, the first light-emitting element 101a and the second light-emitting element 101b emit light beams within different wavelength ranges such as a first light beam within a first wavelength range and a second light beam within a second wavelength range. The light control module 105 controls whether the first light-emitting element 101a and the second light-emitting element 101b are to emit light or not. When the light control module 105 controls the first light-emitting element 101a and the second light-emitting element 101b to emit light, the first light beam and the second light beam are emitted at the same time to provide a mixed light beam. For example, the first light-emitting element 101a emits green light (with a wavelength within 495-570 nm) and the second light-emitting element 101b emits blue light (with a wavelength within 450-475 nm) so that the mixed light beam is cyan. The first light-emitting element 101a and the second light-emitting element 101b are, for example, light-emitting diodes (LEDs).

The light control module 105 can also control the first light-emitting element 101a and the second light-emitting element 101b to emit light in order. For example, after the first light-emitting element 101a emits green light for a period of time, the second light-emitting element 101b is controlled to emit blue light when the first light-emitting element 101a is turned off so as to provide green light and blue light in order. Alternatively, for example, after the first light-emitting element 101a emits green light for a period of time, the second light-emitting element 101b is controlled to emit blue light when the first light-emitting element 101a is still on so as to provide the mixed light beam.

Figure 2:
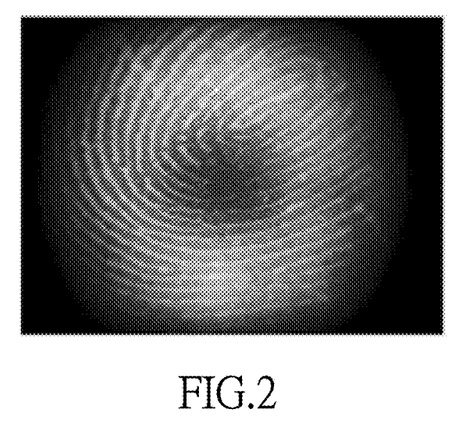
FIG. 2 is a picture of an image signal according to a second embodiment of the present invention.

The image sensing module 103 receives the first light beam and the second light beam reflected by the light guide panel 111. In the present embodiment, the finger 109 touches the light guide panel 111 when the first light-emitting element 101a emits the first light beam. The first light beam is incident on the light guide panel 111 so that part of the first light beam is absorbed by the finger 109 and part of the first light beam is reflected. The image sensing module 103 may provide an image signal corresponding to the finger 109 by the reflected first light beam. FIG. 2 is a picture of an image signal according to a second embodiment of the present invention. With reference to FIG. 1 and FIG. 2, the first light-emitting element 101a emits, for example, a blue light beam onto the light guide panel 111. Since the fingerprint includes ridge peaks and ridge valleys that cause light diffraction, the picture of the image signal, acquired by the image sensing module 103, as shown in FIG. 2 exhibits a series of maxima and minima. Then, an algorithm for fingerprint recognition can be used to acquire the fingerprint of the finger 109 to complete fingerprint recognition.

In one embodiment, after the first light-emitting element 101a emits the first light beam for a period of time, the second light-emitting element 101b is controlled to emit the second light beam. The image sensing module 103 may provide an image signal corresponding to the finger 109 by the mixed light beam including the reflected first light beam and the reflected second light beam.

The analyzing module 107 analyzes the image signal to acquire a physiological signal. In one embodiment, when the first light-emitting element 101a emits the first light beam, the analyzing module 107 extracts and analyzes the image signal within the first wavelength range to acquire a first physiological signal. In another embodiment, the second light-emitting element 101b is controlled to emit the second light beam after the first light-emitting element 101a emits the first light beam for a period of time. The analyzing module 107 extracts and analyzes the image signal within the second wavelength range to acquire a second physiological signal.

With reference to FIG. 1, the first light-emitting element 101a emits blue light and the second light-emitting element 101b emits green light. The image sensing module 103 acquires the blue light reflected by the finger 109, and at the same acquires the green light reflected by a finger vein 109a. Since the first light-emitting element 101a and the second light-emitting element 101b emit light at the same time, the image sensing module 103 acquires an image signal being cyan and delivers the image signal to the analyzing module 107. The analyzing module 107 extracts the image signal being blue from the image signal being cyan to acquire the fingerprint signal.

The palpitant frequency is related to the flow rate of the red blood cells in the finger vein. When the green light enters the finger vein 109a, the reflected green light will be diffracted by the red blood cells. Moreover, the light flux through the finger vein 109a varies due to diastole and systole. Part of the light may be absorbed by the finger vein 109a so that the intensity of the reflected light varies, which corresponds to the palpitant frequency. By analyzing the cycle of the change of light flux with time, the analyzing module 107 can calculate the palpitant frequency. Therefore, the analyzing module 107 can use the image signal to analyze the image signal being green and calculate the cycle of the change of light flux with time to acquire the palpitant frequency signal. When estimating the palpitant frequency, the brightness with respect to time of the image signal is acquired within a sampling time. By comparing the change in brightness of the image signal with respect to time, the time interval between two neighboring peaks or two neighboring valleys of the image signal can be obtained. For example, if the brightness of the current image signal is smaller than the previous image signal, a time interval between two neighboring peaks can be obtained by subtracting the present time by the previous time. Once the cycle of an image signal is acquired, the count of beats per minute can be estimated. In another embodiment for calculating the palpitant frequency, a graph showing the brightness of an image signal as a function of time can be used. The brightness function can be derived by time to estimate the slope. The slope is zero at the peaks or the valleys. For example, the slope of the brightness function decreases to zero at the peaks, while the slope increases to zero at the valleys. Accordingly, when the time interval between two neighboring peaks or two neighboring valleys of the brightness function of the image signal is estimated, the count of beats per minute can be calculated.

In another embodiment, the first light-emitting element 101a or the second light-emitting element 101b may be a red or a near infrared (NIR) light source. Since the blood oxygenation is related to the oxy-hemoglobin concentration in the vein and deoxy-hemoglobin (Hb) and oxy-hemoglobin ($HbO_2$) have different absorption rates with respect to infrared (IR) light or near infrared (NIR) light, blood oxygenation can be calculated by the difference in the reflected light flux.

In the present embodiment, the image signal acquired by the image sensing module 103 is, for example, a multicolored image or a grayscale image. To improve physiological signal recognition, the analyzing module 107 acquires a specific color of an image signal in advance. For example, if the emitted light is green, the analyzing module 107 acquires the green light of the image signal in advance to prevent the recognition of physiological signals from being interfered with by other colors. The analyzing module 107 recognizes the physiological signal by the brightness variation due to absorption of reflected light by the blood or the vein based on the average brightness of the image signal. The average brightness of the image signal is calculated as follows. The brightness of a pixel is taken into account. The analyzing module 107 extracts the green light from the image signal, and sums up the brightness values of the pixels. The total brightness value is then divided by the number of pixels to acquire the average brightness of the image signal. Therefore, by comparing the average brightness of the image signal at two different times, the palpitant frequency and the blood oxygenation can be estimated.

It should be noted that, the physiological signal processing apparatus 10 in one embodiment includes two light-emitting elements. However, according to practical demands, the light-emitting elements can be a blue light-emitting element, a green light-emitting element, a red light-emitting element and/or a near infrared (NIR) light-emitting element. The present invention is not limited to the implementation of the light-emitting element. The wavelength can be adjusted corresponding to specific physiological signals to improve the accuracy in physiological signal recognition.

Furthermore, the image sensing module 103 may acquire a plurality of image signals during a period of sampling time. The brightness function is acquired from the plurality of image signals to recognize physiological signals. Therefore, one embodiment of the present invention provides the user with more flexibility to process the physiological signals by turning on the first light-emitting element 101a and the second light-emitting element 101b in sequence according to practical demands.

One embodiment of the present invention uses different colored light beams to acquire or recognize physiological signals. The image signal acquired by different colored light beams (within different wavelength ranges) exhibits higher efficiency in recognizing the physiological signals. For example, blue light is preferred in recognizing a fingerprint because the reflected blue light exhibits higher contrast between the minima and the maxima than other colored light beams; green light is preferred in recognizing the palpitant frequency because the reflected green light exhibits larger variation in light flux than other colored light beams; and red or near infrared (NIR) light is preferred in recognizing blood oxygenation because the reflected red or near infrared (NIR) light exhibits larger variation in light flux than other colored light beams.

Figure 3:
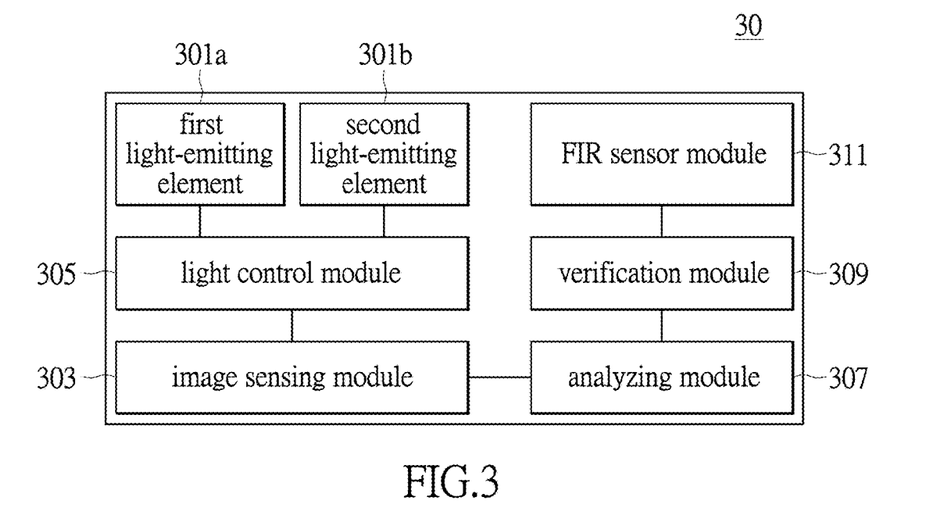
FIG. 3 is a block diagram of a physiological signal processing apparatus according to a third embodiment of the present invention.

FIG. 3 is a block diagram of a physiological signal processing apparatus according to a third embodiment of the present invention. With reference to FIG. 3, the physiological signal processing apparatus 30 includes a first light-emitting element 301a, a second light-emitting element 301b, a light control module 305, an image sensing module 303, an analyzing module 307, a verification module 309 and an FIR sensor module 311. The first light-emitting element 301a, the second light-emitting element 301b, the light control module 305, the image sensing module 305 and the analyzing module 307 are similar to the first light-emitting element 101a, the second light-emitting element 101b, the light control module 105, the image sensing module 103 and the analyzing module 107 in FIG. 1. Accordingly, detailed descriptions thereof are not redundantly repeated herein.

The verification module 309 is coupled to the analyzing module 307 and the FIR sensor module 311. The verification module 309 decides whether the first physiological signal conforms to the identification data recorded in the database. For example, the fingerprint of a user is recorded in the verification module 309. When the first physiological signal is a fingerprint signal, the verification module 309 decides whether the acquired fingerprint signal conforms to the valid fingerprint of the user. After the verification module 309 decides whether the acquired fingerprint signal conforms to the valid fingerprint recorded in the database, verification is completed and a command is further triggered for deciding or providing a second physiological signal.

Furthermore, after the verification module 309 in one embodiment of the present invention decides the fingerprint signal is valid and acquires the second physiological signal, the verification module 309 may decide whether the first physiological signal is true or false according to the second physiological signal. For example, the second physiological signal is the palpitant frequency or the blood oxygenation. Even though the normal palpitant frequency or blood oxygenation exhibits steady fluctuations, there are small differences between the fluctuations. The verification module 309 may decide whether the second physiological signal is true or false based on whether the palpitant frequency or the blood oxygenation is too regular or whether there are reasonable physiological characteristics to decide whether the second physiological signal is true or false. Under the circumstances that the second physiological signal is decided to be false, the first physiological signal is also decided to be false. Otherwise, even though the analyzing module 307 fails to acquire the second physiological signal, the verification module 309 may decide the first physiological signal to be false.

The FIR sensor module 311 may be used for acquiring the temperature of a finger. In one embodiment, after the verification module 309 decides that the first physiological signal conforms to the identification data recorded in the database, the FIR sensor module starts sensing the temperature. The FIR sensor module 311 is, for example, an FIR sensor that is capable of sensing FIR light emitted from the human body so as to determine the variation of the body temperature with respect to the wavelength offset of the received light.

The physiological signal processing apparatus according to one embodiment of the present invention may not only recognize or acquire a plurality of physiological signals, but also decides whether the fingerprint signal is true or false based on the palpitant frequency or the blood oxygenation. Accordingly, the physiological signal processing apparatus according to one embodiment of the present invention provides improved accuracy for fingerprint recognition using light beams with specific wavelengths and improved verification security to avoid false fingerprints from being verified.

Figure 4:
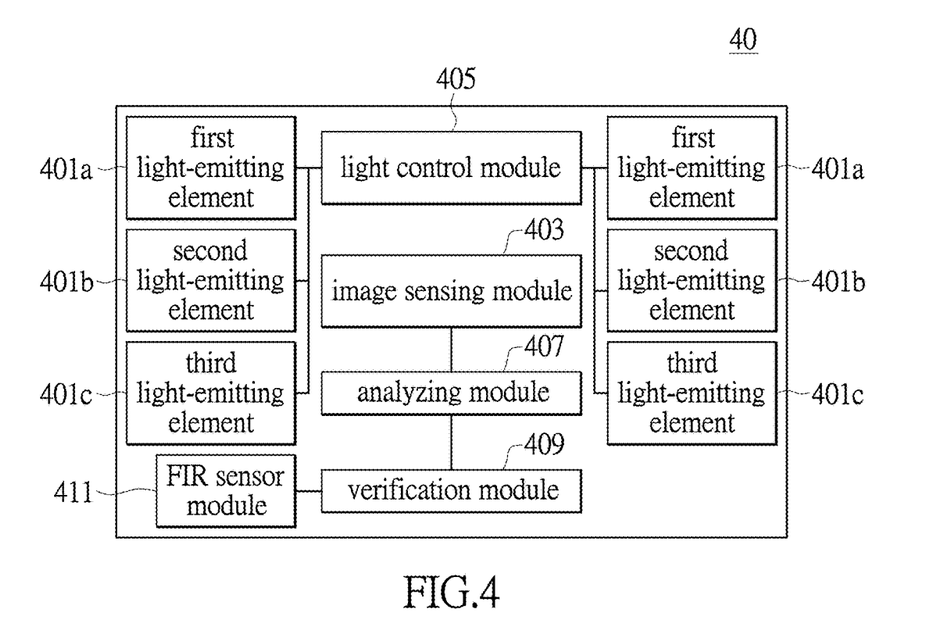
FIG. 4 is a block diagram of a physiological signal processing apparatus according to a fourth embodiment of the present invention.

FIG. 4 is a block diagram of a physiological signal processing apparatus according to a fourth embodiment of the present invention. With reference to FIG. 4, the physiological signal processing apparatus 40 includes at least one first light-emitting element 401a, at least one second light-emitting element 401b, at least one third light-emitting element 401c, an image sensing module 403, a light control module 405, an FIR sensor module 407 and a verification module 409. The first light-emitting element 401a, the second light-emitting element 401b and the third light-emitting element 401c are respectively coupled to the light control module 405. The analyzing module 407 is coupled to the image sensing module 403 and the verification module 409. The verification module 409 is coupled to the FIR sensor module 407.

The physiological signal processing apparatus 40 is different from the physiological signal processing apparatus 30 in that the physiological signal processing apparatus 40 includes three light-emitting elements capable of emitting different colored light beams. More particularly, the physiological signal processing apparatus 40 may include at least one of each of the three light-emitting elements capable of emitting different colored light beams. The light-emitting elements may be disposed on both sides of the physiological signal processing apparatus 40. For example, the first light-emitting element 401a is a blue light-emitting element, the second light-emitting element 401b is a green light-emitting element and the third light-emitting element 401c is a red light-emitting element. The light control module 405 controls whether each of the light-emitting elements to emit light to provide a mixed light beam so that the image sensing module 403 acquires an image signal based on the reflected mixed light beam. Then, the analyzing module 407 analyzes the image signal to provide three physiological signals. The analyzing module 407 analyzes the image signal extracted by the first light beam (for example, blue light) to acquire a first physiological signal, analyzes the image signal extracted by the second light beam (for example, green light) to acquire a second physiological signal, and analyzes the image signal extracted by the third light beam (for example, red light) to acquire a third physiological signal. Taking the first light beam being blue light for example, the analyzing module 407 extracts an image signal being blue from the image signal to acquire the first physiological signal according to the extracted image signal.

The physiological signal processing apparatus 40 may acquire a plurality of physiological signals at the same time and improve the accuracy for physiological signal recognition to prevent signal interference by other colored beams by providing a plurality of light-emitting elements to emit light beams within the same wavelength range.

(Another Embodiment of Physiological Signal Processing Apparatus)

Figure 5:
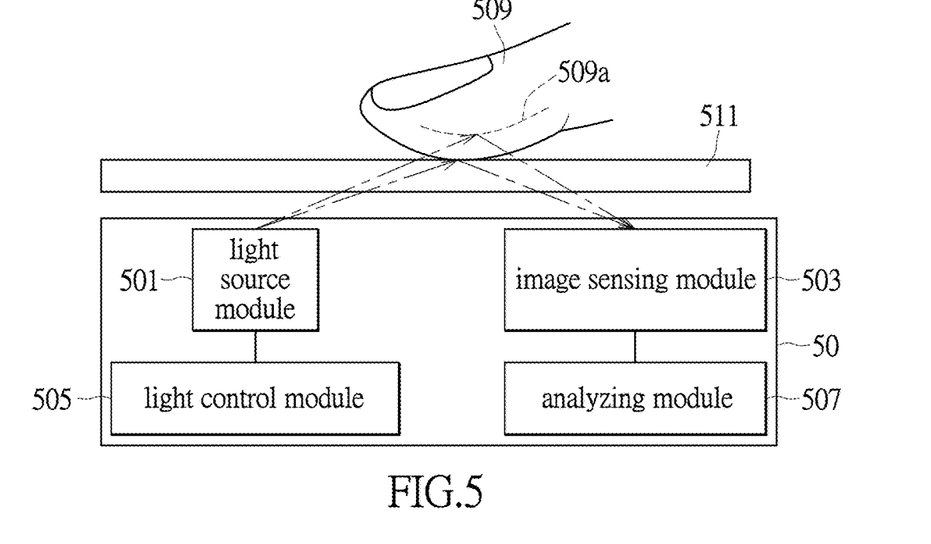
FIG. 5 is a schematic diagram of a physiological signal processing apparatus according to a fifth embodiment of the present invention.

FIG. 5 is a schematic diagram of a physiological signal processing apparatus according to a fifth embodiment of the present invention. With reference to FIG. 5, the physiological signal processing apparatus 50 includes a light source module 501, a light control module 505, an image sensing module 503 and an analyzing module 507. The light source module 501 is coupled to the light control module 505. The image sensing module 503 is coupled to the analyzing module 507. The physiological signal processing apparatus 50 includes a light guide panel 511 for a finger 109 of the user to touch. The light source module 501 is disposed opposite to where the finger 509 touches the light guide panel 511.

The light source module 501 is capable of emitting a plurality of light beams. For example, the light beams within different wavelength ranges are blue light, green light and red light. The light control module 505 controls the light source module 501 to emit light beams. The image sensing module 503 senses the light emitted from the light source module 501 and reflected by the light guide panel 511 to acquire an image signal of the finger 509, for example, the skin or the vein 509a of the finger 509. The analyzing module 507 analyzes the image signal extracted by the light beams (for example, the light beams within different wavelength ranges) respectively, and provides a plurality of physiological signals accordingly. The light source module 501 is, for example, a three primary color light-emitting diode. Similar elements have been described above and thus the description of the light source module 501 is not redundantly repeated herein. Practically, the physiological signal processing apparatus 50 may employ suitable light sources according to the demands to improve the recognition of physiological signals.

Figure 6:
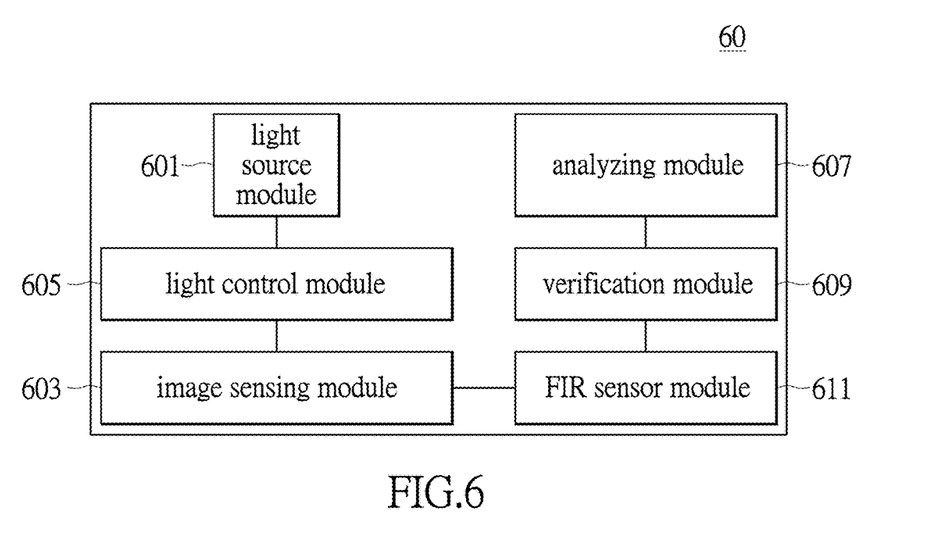
FIG. 6 is a block diagram of a physiological signal processing apparatus according to a sixth embodiment of the present invention.

FIG. 6 is a block diagram of a physiological signal processing apparatus according to a sixth embodiment of the present invention. With reference to FIG. 6, the physiological signal processing apparatus 60 includes a light source module 601, a light control module 605, an image sensing module 603, an analyzing module 607, a verification module 609 and an FIR sensor module 611. The physiological signal processing apparatus 60 is different from the physiological signal processing apparatus 50 in that the physiological signal processing apparatus 60 further includes a verification module 609 and an FIR sensor module 611. The light control module 605 is coupled to the light source module 601 and the image sensing module 603. The verification module 609 is coupled to the analyzing module 607 and the FIR sensor module 611. Similar elements have been described above and thus the description of the other elements of the physiological signal processing apparatus 60 is not redundantly repeated herein.

Figure 7:
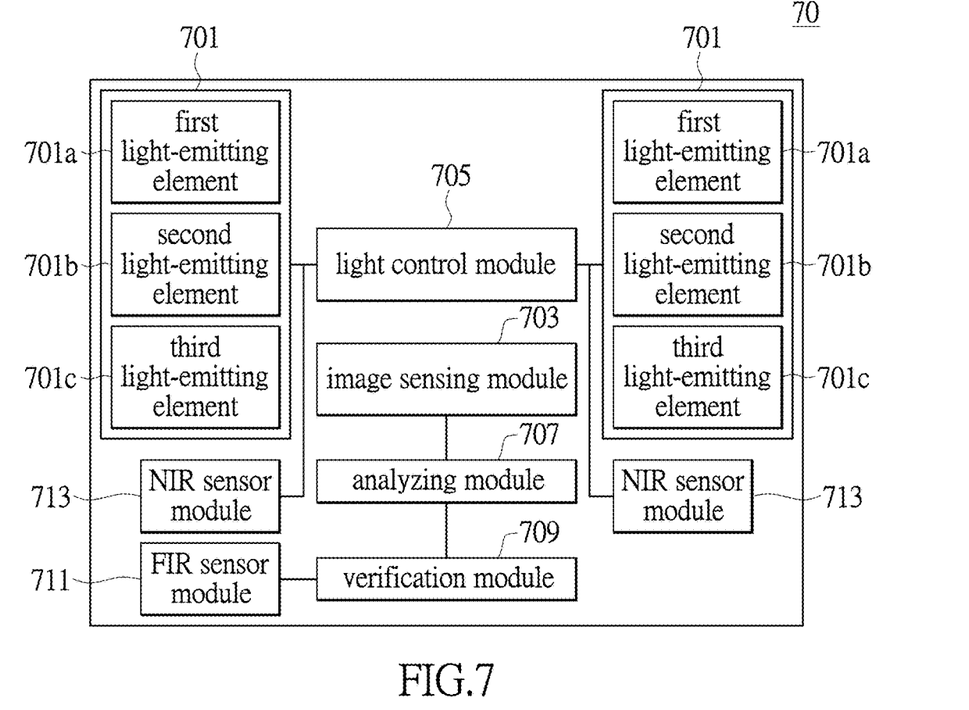
FIG. 7 is a block diagram of a physiological signal processing apparatus according to a seventh embodiment of the present invention.

FIG. 7 is a block diagram of a physiological signal processing apparatus according to a seventh embodiment of the present invention. With reference to FIG. 7, the physiological signal processing apparatus 70 includes a light source module 701, a light control module 705, an image sensing module 703, an analyzing module 707, a verification module 709, an FIR sensor module 711 and an NIR light-emitting element 713. The light source module 701 includes a first light-emitting element 701a, a second light-emitting element 701b and a third light-emitting element 701c. The light source module 701 and the NIR light-emitting element 713 are coupled to the light control module 705. The analyzing module 707 is coupled to the image sensing module 703 and the verification module 709. The verification module 709 is coupled to the FIR sensor module 711.

The light source module 701 is a light-emitting element module capable of emitting one or more light beams. The light source module 701 includes, for example, a blue light-emitting element, a green light-emitting element and/or a red light-emitting element capable of emitting light beams within the same or different wavelength ranges. The light source module 701 is controlled by the light control module 705 to emit at least one of blue light, green light and red light. In another embodiment, a white light-emitting element may be available by packaging a blue light-emitting element with phosphors. In another embodiment, the light source module 701 may include three light-emitting elements, each being capable of emitting light within the same or different wavelength ranges. For example, the first light-emitting element 701a, the second light-emitting element 701b and the third light-emitting element 701c may all be white light-emitting elements. Alternatively, the first light-emitting element 701a is a blue light-emitting element, the second light-emitting element 701b is a green light-emitting element and the third light-emitting element 701c is a red light-emitting element. Accordingly, the light source module 701 may be a three primary color light-emitting element, for example, a three primary color light-emitting diode (RGB LED). Practically, the first light-emitting element 701a, the second light-emitting element 701b and the third light-emitting element 701c are integrated in one package. In the physiological signal processing apparatus 70, the light control module 705 controls the first light-emitting element 701a, the second light-emitting element 701b and the third light-emitting element 701c to emit light in sequence according to practical demands. Accordingly, the recognition of physiological signals may be improved with less light-emitting elements.

The light control module 705 may control the light source module 701 to emit different light beams within different wavelength ranges, such as blue light, green light, red light or white light. In the embodiment where the light source module 701 is a three primary color light-emitting element, the light control module 705 controls the first light-emitting element 701a, the second light-emitting element 701b and the third light-emitting element 701c to respectively emit blue light, green light and red light at the same time. With reference to FIG. 5 and FIG. 7, the image sensing module 703 senses the RGB mixed light beam reflected by the skin and the vein 509a of the finger 509 to acquire an original image signal, which is, for example, an image signal based on the reflected white light. The analyzing module 707 extracts different colored images from the original image signal, and analyzes the different colored images to provide corresponding physiological signals. For example, the analyzing module 707 extracts a blue image signal from the image signal, and analyzes the blue image signal to acquire the fingerprint signal. The analyzing module 707 extracts a green image signal from the image signal, and analyzes the green image signal to acquire the palpitant frequency signal. The analyzing module 707 extracts a red image signal from the image signal, and analyzes the red image signal to acquire the blood oxygenation signal.

The NIR light-emitting element 713 emits near infrared light. The image sensing module 703 acquires a near infrared image signal, and the analyzing module 705 analyzes the near infrared image signal to acquire the blood oxygenation signal. Similar elements have been described above and thus the description of the other elements of the physiological signal processing apparatus 70 is not redundantly repeated herein.

Therefore, in the physiological signal processing apparatus 70 according to one embodiment of the present invention, the light control module 705 controls the light source module 701 to emit light to enhance the efficiency of acquiring physiological signals. For example, when the light control module 705 controls the light source module 701 to emit two colored light beams so that the image sensing module 703 acquires the image signal based on the two colored light beams, the analyzing module 707 analyzes the image signal extracted by the two colored light beams respectively to acquire two physiological signals. In another embodiment, the light control module 705 may also control the light source module 701 to emit three colored light beams so that the image sensing module 703 acquires the image signal based on the three colored light beams. The analyzing module 707 analyzes the image signal extracted by the three colored light beams respectively to acquire three physiological signals.

It should be noted that, in one embodiment of the present invention, light beams within different wavelength ranges are employed to acquire and recognize physiological signals. When recognizing the physiological signals, the analyzing module 707 employs the different colored image signals to enhance the efficiency in recognizing physiological signals. For example, blue light or green light is preferred in recognizing a fingerprint because the reflected blue or green light exhibits higher contrast between the minima and the maxima than other colored light beams; and blue light or green light is preferred in recognizing the palpitant frequency because the reflected blue light or green light exhibits larger variation in light flux than other colored light beams. Therefore, in one embodiment of the present invention, light beams within different wavelength ranges are emitted to the finger to enhance the efficiency of recognizing physiological signals by the analyzing module 707.

(Embodiment of Physiological Signal Processing Method)

Figure 8:
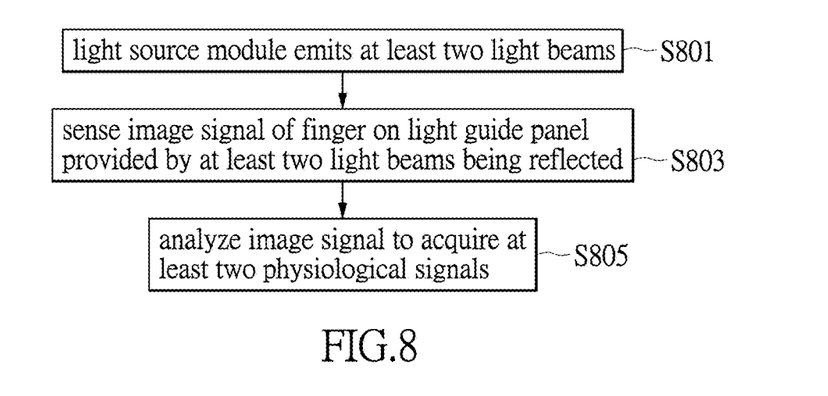
FIG. 8 is a flowchart of a physiological signal processing method according to an eighth embodiment of the present invention.

FIG. 8 is a flowchart of a physiological signal processing method according to an eighth embodiment of the present invention. With reference to FIG. 8, the physiological signal processing method in one embodiment of the present invention is applicable to the physiological signal processing apparatus 60. In step S801, the light source module emits at least two light beams (for example, two colored light beams within different wavelength ranges) onto a light guide panel of the physiological signal processing apparatus.

In step S803, the image sensing module acquires an image signal of a finger on a light guide panel provided by a mixed light beam including at least two light beams (for example, two colored light beams within two wavelength ranges) being reflected. In step S805, the analyzing module analyzes the image signal to acquire at least two physiological signals. When the analyzing module analyzes the image signal, the light beams within different wavelength ranges or within a specific wavelength range are acquired on the image signal in advance to obtain two color images. Then, the two color images are respectively processed to obtain two physiological signals. Furthermore, after the analyzing module acquires the two physiological signals, the verification module can, according to one of the physiological signals, decide whether another physiological signal is true or false.

As stated above, in one embodiment of the present invention, the physiological signal processing apparatus and the physiological signal processing method control the different colored light beams emitted onto the light guide panel. The analyzing module analyzes the physiological signal from the image signal and the features of the physiological signal may be emphasized by the use of the different colored light beams to improve the recognition of physiological signals. Furthermore, in one embodiment of the present invention, the physiological signal processing apparatus can recognize at least two physiological signals to provide better recognition and false proof. Furthermore, in one embodiment of the present invention, the plurality of light-emitting elements, the image sensing module and the analyzing module can be packaged in the physiological signal processing apparatus so as to downsize the currently available physiological signal recognition apparatus and further simplify the apparatus structure with lowered material cost.

The above-mentioned descriptions represent merely the exemplary embodiment of the present disclosure, without any intention to limit the scope of the present disclosure thereto. Various equivalent changes, alterations or modifications based on the claims of present disclosure are all consequently viewed as being embraced by the scope of the present disclosure.

What is claimed is:

1. A physiological signal processing apparatus, comprising:
    a first light-emitting element capable of emitting a first light beam and a second light-emitting element capable of emitting a second light beam, said first light-emitting element and said second light-emitting element emitting said first light beam and said second light beam on a light guide panel for a finger to touch, wherein said first light-emitting element and said second light-emitting element are disposed opposite to where said finger touches said light guide panel;
    a light control module controlling said first light-emitting element and said second light-emitting element to emit said first light beam and said second light beam;
    an image sensing module sensing said first light beam and said second light beam reflected by said light guide panel to provide an image signal of said finger;
    an analyzing module analyzing said image signal extracted by said first light beam to acquire a first physiological signal, and analyzing said image signal extracted by said second light beam to acquire a second physiological signal, wherein said first physiological signal is different from said second physiological signal; and
    a far infrared sensor module sensing said finger to acquire a temperature of said finger;
    wherein said far infrared sensor module acquires the temperature of said finger after a verification module decides whether said first physiological signal conforms to identification data recorded in a database.

2. The physiological signal processing apparatus of claim 1, further comprising a verification module coupled to said analyzing module and said far infrared sensor module to decide whether said first physiological signal conforms to identification data that is valid, and decide whether said first physiological signal is true or false according to said second physiological signal.

3. The physiological signal processing apparatus of claim 2, wherein said first light-emitting element is a blue light-emitting element, a green light-emitting element or a white light-emitting element, said second light-emitting element is a blue light-emitting element, a green light-emitting element or a red light-emitting element.

4. The physiological signal processing apparatus of claim 1, wherein said first physiological signal is a fingerprint signal or a palpitant frequency, and said second physiological signal is a fingerprint signal, a palpitant frequency signal or a blood oxygenation signal.

5. The physiological signal processing apparatus of claim 1, further comprising a third light-emitting element, said third light-emitting element being controlled by said light control module to emit a third light beam, and said first light-emitting element being a blue light-emitting element, said second light-emitting element being a green light-emitting element and said third light-emitting element being a red light-emitting element.

6. A physiological signal processing apparatus, comprising:
    a light source module capable of emitting a mixed light beam on a light guide panel for a finger to touch, wherein said light source module is disposed opposite to where said finger touches said light guide panel and said mixed light beam comprises a plurality of colored light beams;
    a light control module coupled to said light source module and controlling said light source module to emit said mixed light beam;
    an image sensing module sensing said mixed light beam reflected by said light guide panel to provide an image signal of said finger;
    an analyzing module coupled to said image sensing module and analyzing said image signal extracted by any of said plurality of colored light beams to acquire a plurality of physiological signals; and
    a far infrared sensor module sensing said finger to acquire a temperature of said finger;
    wherein said far infrared sensor module acquires the temperature of said finger after a verification module decides whether one of said physiological signals conforms to identification data recorded in a database.

7. The physiological signal processing apparatus of claim 6, wherein said light control module controls said light source module to emit two colored light beams so that said image sensing module acquires said image signal reflected by said two colored light beams, wherein said analyzing module analyzes said image signal extracted by any of said two colored light beams to acquire two physiological signals.

8. The physiological signal processing apparatus of claim 6, wherein said light control module controls said light source module to emit three colored light beams so that said image sensing module acquires said image signal reflected by said three colored light beams, wherein said analyzing module analyzes said image signal extracted by any of said three colored light beams to acquire three physiological signals.

9. The physiological signal processing apparatus of claim 8, further comprising a verification module coupled to said analyzing module and said far infrared sensor module to decide whether one of said physiological signals provided by said analyzing module conforms to identification data recorded in a database, and decide whether said physiological signal that conform to said identification data is true or false according to any of said physiological signals.

10. The physiological signal processing apparatus of claim 6, wherein said light source module is a three primary color light-emitting diode or a white light-emitting diode.

11. A physiological signal processing method applicable to a physiological signal processing apparatus, said physiological signal processing apparatus comprising an image sensing module, said method comprising the steps of:

emitting at least one first light beam and at least one second light beam;

sensing an image signal of a finger on a light guide panel of said physiological signal processing apparatus by said image sensing module, said image signal being provided by said first light beam and said second light beam being reflected;

analyzing said image signal to acquire at least one first physiological signal and at least one second physiological signal, wherein said first physiological signal is different from said second physiological signal; and sensing said finger by a far infrared sensor module to acquire a temperature of said finger;

wherein said far infrared sensor module acquires the temperature of said finger after a verification module decides whether said first physiological signal conforms to identification data recorded in a database.

12. The physiological signal processing method of claim 11, wherein said step of analyzing said image signal comprises, extracting a first image signal within a first wavelength range from said image signal to acquire said first physiological signal, and extracting a second image signal within a second wavelength range from said image signal to acquire said second physiological signal.

13. The physiological signal processing method of claim 12, further comprising:

deciding whether said first physiological signal is true or false according to whether said second physiological signal is true or false after deciding that said first physiological signal conforms to identification data that is valid.

14. The physiological signal processing method of claim 13, wherein whether said second physiological signal is true or false is decided based on whether said second physiological characteristics are real physiological characteristics or not.

15. The physiological signal processing method of claim 14, wherein said first physiological signal is decided to be false when said second physiological signal is decided to be false.

16. The physiological signal processing method of claim 14, wherein said first physiological signal is a fingerprint signal, and said second physiological signal is a palpitant frequency signal or a blood oxygenation signal.

17. The physiological signal processing method of claim 16, wherein said palpitant frequency signal or said blood oxygenation signal is acquired by calculating according to the brightness and the response time of said image signal acquired within a sampling time.

18. The physiological signal processing method of claim 11, wherein said first light beam and said second light beam are emitted by a first light-emitting element and a second light-emitting element, or a three primary color light-emitting diode.

* * * * *